(12) United States Patent
Yoo et al.

(10) Patent No.: US 11,266,340 B2
(45) Date of Patent: Mar. 8, 2022

(54) MULTI-CHANNEL SCALABLE EEG ACQUISITION SYSTEM ON A CHIP WITH INTEGRATED PATIENT SPECIFIC SEIZURE CLASSIFICATION AND RECORDING PROCESSOR

(71) Applicants: Massachusetts Institute of Technology, Cambridge, MA (US); Khalifa University of Science and Technology, Abu Dhabi (AE)

(72) Inventors: Jerald Yoo, Abu Dhabi (AE); Anantha P. Chandrakasan, Belmont, MA (US); Long Yan, Leuven (BE); Dina Reda El-Damak, Cambridge, MA (US); Ali Hossam Shoeb, Walnut Creek, CA (US); Muhammad Awais Bin Altaf, Abu Dhabi (AE)

(73) Assignees: MASSACHUSETTS INSTITUTE OF TECHNOLOGY, Cambridge, MA (US); KHALIFA UNIVERSITY OF SCIENCE AND TECHNOLOGY

( * ) Notice: Subject to any disclaimer, the term of this patent is extended or adjusted under 35 U.S.C. 154(b) by 370 days.

(21) Appl. No.: 15/955,010

(22) Filed: Apr. 17, 2018

(65) Prior Publication Data
US 2018/0303364 A1 Oct. 25, 2018

Related U.S. Application Data

(63) Continuation of application No. 14/378,833, filed as application No. PCT/US2013/026389 on Feb. 15, 2013, now abandoned.

(Continued)

(51) Int. Cl.
*A61B 5/316* (2021.01)
*A61B 5/369* (2021.01)
(Continued)

(52) U.S. Cl.
CPC .............. *A61B 5/316* (2021.01); *A61B 5/369* (2021.01); *A61B 5/4094* (2013.01); *H03F 3/387* (2013.01);
(Continued)

(58) Field of Classification Search
CPC . A61B 5/04012; A61B 5/0476; A61B 5/4094; A61B 2562/166; H03F 3/387;
(Continued)

(56) References Cited

U.S. PATENT DOCUMENTS

2002/0145970 A1* 10/2002 Han .......................... H04L 5/06
370/206
2005/0215916 A1* 9/2005 Fadem ................. A61B 5/6814
600/544
(Continued)

*Primary Examiner* — Navin Natnithithadha
(74) *Attorney, Agent, or Firm* — K&L Gates LLP (57) ABSTRACT

An integrated circuit chip and method for EEG monitoring. In one embodiment, the integrated circuit chip includes an Analog Front End cell in communication with an electrode and a Classification Processor wherein a signal received from the electrode is processed by the Classification Engine cell and designated as seizure or non-seizure. In another embodiment, the Analog Front End cell includes an amplifier cell in communication with an electrode; and an ASPU cell in communication with the amplifier cell. In yet another embodiment, the Classification Processor includes a DBE Channel Controller cell; a Feature Extraction Engine Processor cell, and a Classification Engine cell in communication with the Feature Extraction Engine Processor cells and the DBE Channel Controller cell.

25 Claims, 8 Drawing Sheets

Related U.S. Application Data

(60) Provisional application No. 61/600,369, filed on Feb. 17, 2012.

(51) Int. Cl.
*H03F 3/387* (2006.01)
*A61B 5/00* (2006.01)
*H03H 17/02* (2006.01)

(52) U.S. Cl.
CPC .... *H03H 17/0226* (2013.01); *H03H 17/0248* (2013.01); *A61B 2562/166* (2013.01); *H03F 2200/294* (2013.01); *H03F 2200/375* (2013.01)

(58) Field of Classification Search
CPC ........ H03F 2200/294; H03F 2200/375; H03H 17/0226; H03H 17/0248
USPC .................................................. 600/544, 545
See application file for complete search history.

(56) References Cited

U.S. PATENT DOCUMENTS

| | | | | |
|---|---|---|---|---|
| 2009/0082691 A1* | 3/2009 | Denison | ............. | A61B 5/04004 |
| | | | | 600/544 |
| 2010/0280579 A1* | 11/2010 | Denison | ............. | A61N 1/36082 |
| | | | | 607/62 |
| 2011/0193623 A1* | 8/2011 | Yazicioglu | .......... | H03F 3/45479 |
| | | | | 330/103 |

* cited by examiner

000
MULTI-CHANNEL SCALABLE EEG ACQUISITION SYSTEM ON A CHIP WITH INTEGRATED PATIENT SPECIFIC SEIZURE CLASSIFICATION AND RECORDING PROCESSOR

RELATED APPLICATIONS

This application claims priority to U.S. Provisional Patent Application 61/600,369 filed Feb. 17, 2012, the contents of which are herein incorporated by reference in their entirety.

FIELD OF THE INVENTION

The invention relates generally to the field of vital signs monitoring and specifically to the field of electroencephalogram (EEG) monitoring.

BACKGROUND OF THE INVENTION

Tracking seizure activity in order to provide proper medication requires a device having a small form factor, and ultra-low power sensors with continuous EEG classification. Technical challenges arise from 1) patient-to-patient variation of a seizure pattern on EEG, 2) fully integrating ultra-low power variable dynamic range instrumentation circuits with a seizure detection processor, and 3) reducing communication overhead. One prior device extracted EEG features locally on-chip to reduce the data being transmitted, and saved power by $\frac{1}{14}$ when compared to raw EEG data transmission. However, that device still needed data transmission and off-chip classification to detect and to store seizure activity.

What is needed is an ultra-low power scalable EEG acquisition System on a Chip (SoC) for continuous seizure detection and recording with a fully integrated patient-specific Support Vector Machine (SVM)-based classification processor.

The present invention addresses this need.

SUMMARY OF THE INVENTION

In one aspect, the invention relates to an integrated circuit chip for EEG monitoring. In one embodiment, the integrated circuit chip for EEG monitoring includes: an Analog Front End cell, the Analog Front End cell includes: an amplifier cell in communication with an EEG electrode; an analog signal processing unit (ASPU) cell in communication with the amplifier cell; and a Classification Processor including: a digital back end (DBE) Channel Controller cell; a Feature Extraction Engine Processor cell, the Feature Extraction Engine Processor cell in communication with the DBE Channel Controller cell and the Analog Front End cell; and a Classification Engine cell in communication with the Feature Extraction Engine Processor cell and the DBE Channel Controller cell, wherein a signal received from the electrode is processed by the Classification Engine cell and designated as seizure or non-seizure. In another embodiment, the amplifier cell in communication with the electrode is a Chopper Stabilized-Capacitive Coupled Instrumentation Amplifier (CS-CCIA) cell. In yet another embodiment, the amplifier cell in communication with the electrode is an autozeroing amplifier circuit cell. In still yet another embodiment, the Feature Extraction Engine Processor cell includes: a plurality of bandpass filter cells, each bandpass filter cell in communication with the ASPU cell; and a plurality of integrator cells, each integrator cell in communication with a respective one of the plurality of bandpass filter cells; wherein a signal from the ASPU cell of an Analog Front End is filtered by a plurality of bandpass filters to form a plurality of sub-bands, and wherein each of the sub-bands is integrated by a respective one of the plurality of integrator cells to determine the energy of the sub-band.

In one embodiment, the Feature Extraction Engine Processor cell further includes: a decimation filter cell in communication between the ASPU cell and the plurality of bandpass filter cells, and wherein a signal from the ASPU cell of an Analog Front End is decimated by the decimation cell prior to being filtered by the plurality of bandpass filter cells. In another embodiment, the integrated sub-bands are aggregated to form a feature vector. In yet another embodiment, Classification Engine cell designates the signal received from the electrode as a seizure condition or a non-seizure condition in response to the feature vector. In still yet another embodiment, the integrated circuit chip further includes an analog to digital converter cell in communication with the ASPU cell and the Feature Extraction cell. In one embodiment, the analog to digital converter cell in communication with the ASPU cell and the Feature extraction cell is a Successive-approximation-register (SAR) analog-to-digital converters (ADC). In another embodiment, the Classification Engine includes an SVM and the SVM designates the signal, received from the electrode, as seizure or non-seizure in response to the feature vector, by determining on which side of a hyperplane in feature hyperspace the feature vector lies. In yet another embodiment, the Analog Front End cell is a plurality of Analog Front End cells, wherein the Feature Extraction Engine cell is a plurality of Feature Extraction Engine cells, and wherein each Feature Extraction Engine cell is in communication with a respective one of the Analog Front End cells. In still yet another embodiment, the integrated circuit chip further includes: a multiplexer cell in communication with the plurality of Analog Front End cells; and an ADC cell in communication with the multiplexer cell and the plurality of Feature Extraction Engine processor cells. In another embodiment, the ADC cell is an SAR cell.

In yet another embodiment, the DBE Channel controller includes: a channel gain control line and a channel bandwidth control line in communication with an Analog Front End cell. In still yet another embodiment, the DBE Channel Controller includes a channel gain control line, a channel bandwidth control line, and a channel number select in communication with the Analog Front End (AFE)_Channel Controllers and a channel select control line in communication with the multiplexer cell, wherein the DBE Channel Controller is in communication with an external data interface, and wherein the DBE Channel Controller selects the number of channel to be used in response to receiving the number of channels from the external data interface and setting the respective AFE Channel Controller on or off. In another embodiment, each bandpass filter comprises: a plurality of Look Up Tables (LUTs), each LUT having a plurality of inputs and having an output, a plurality of bit shift registers, each bit shift register having an input in communication with the ASPU and an output in communication with a respective input of the LUT; a summer having a first input in communication with the output of the LUT and having a second input and an output; and a register having an input in communication with the output of the summer and having an output in communication with the second input of the summer; wherein the output of the bandpass filter is the output of the register. In yet another embodiment, LUT is a distributed quad-LUT. In still yet another embodiment, the CS-CCIA includes: an input-chopped switch having an input in communication with the electrode and having an output; a low noise amplifier having an input in communication with the output of the input-chopped switch and an first output connected to an input of the ASPU and having a second output; an Impedance Boosting Loop including a IBL chopper switch having an input in communication with the low noise amplifier output and an output in communication with the low noise amplifier input; a Direct Current (DC) Servo Loop including: a DC Servo Loop (DSL) amplifier having an input in communication with the output of the low noise amplifier; a DSL chopper switch having an input in communication with the output of the DSL amplifier and a output in communication with the input of the low noise amplifier; and an Offset Cancellation Loop (OCL) including: an OCL amplifier having an input in communication with the second output of the low noise amplifier and having an output; an OCL chopped switch having an input in communication with the output of the OCL amplifier and having an output; a high pass filter having an input in communication with the output of the OCL chopped switch and having an output; and an gain chopped switch having an input in communication with the output of the high pass filter and having an output in communication with the input of the low noise amplifier.

In one embodiment, the autozeroing amplifier circuit cell includes: an auto zero amplifier having an input in communication with the electrode and having an output; a low noise amplifier having an input in communication with the output of the autozero amplifier and an first output connected to an input of the ASPU and having a second output; an Impedance Boosting Loop including a IBL chopper switch having an input in communication with the low noise amplifier output and an output in communication with the low noise amplifier input; a DC Servo Loop including: a DSL amplifier having an input in communication with the output of the low noise amplifier; a DSL chopper switch having an input in communication with the output of the DSL amplifier and a output in communication with the input of the low noise amplifier; and an Offset Cancellation Loop including: an OCL amplifier having an input in communication with the second output of the low noise amplifier and having an output; an OCL chopped switch having an input in communication with the output of the OCL amplifier and having an output; a high pass filter having an input in communication with the output of the OCL chopped switch and having an output; and an gain chopped switch having an input in communication with the output of the high pass filter and having an output in communication with the input of the low noise amplifier. In another embodiment, the integrated circuit chip further includes: a bus; an Static random-access memory (SRAM) in communication with the bus; an external memory interface in communication with the bus; and an external data interface in communication with the bus; wherein the bus is in communication with the Classification Processor.

In another aspect, the invention relates to a method for monitoring an EEG using an integrated circuit chip. In one embodiment, the method for monitoring an EEG using an integrated circuit chip includes the steps of: amplifying a signal from an EEG electrode to generate an amplified EEG signal; adapting the gain of the amplified EEG signal using an ASPU; digitizing the adapted gain signal using an analog to digital converter; extracting a feature vector from the digitized adapted gain signal using a feature extraction engine; and designating the feature vector as seizure or non-seizure using a classification engine. In another embodiment, the step of adapting the gain of the amplified EEG signal occurs in real-time. In another embodiment, the step of extracting a feature vector includes the steps of: dividing the digitized adapted gain signal into a plurality of sub-bands; integrating each sub-band to calculate the energy within each sub-band; and aggregating each integrated sub-band to generate a feature vector. In still yet another embodiment, the step of designating the feature vector as seizure or non-seizure includes the steps of: generating, in response to patient data, a hyperplane separating a seizure region of feature hyperspace from a non-seizure region of feature hyperspace; and determining in which region of feature hyperspace the feature vector exists. In another embodiment, the step of dividing the digitized adapted gain signal into a plurality of sub-bands utilizes a LUT.

In yet another aspect, the invention relates to a CS-CCIA. In one embodiment, the CS-CCIA includes: an input-chopped switch having an input in communication with a signal source and having an output; a low noise amplifier having an input in communication with the output of the input-chopped switch and an first output connected to an input of the ASPU and having a second output; an Impedance Boosting Loop including a IBL chopper switch having an input in communication with the low noise amplifier output and an output in communication with the low noise amplifier input; a DC Servo Loop including: a DSL amplifier having an input in communication with the output of the low noise amplifier; a DSL chopper switch having an input in communication with the output of the DSL amplifier and a output in communication with the input of the low noise amplifier; and an Offset Cancellation Loop including: an OCL amplifier having an input in communication with the second output of the low noise amplifier and having an output; an OCL chopped switch having an input in communication with the output of the OCL amplifier and having an output; a high pass filter having an input in communication with the output of the OCL chopped switch and having an output; and an gain chopped switch having an input in communication with the output of the high pass filter and having an output in communication with the input of the low noise amplifier. In another embodiment, the Impedance Boosting Loop comprises a IBL chopper switch having an input in communication with the low noise amplifier output and an output in communication with the low noise amplifier input. In yet another embodiment, the DC Servo Loop includes: a DSL amplifier having an input in communication with the output of the low noise amplifier; a DSL chopper switch having an input in communication with the output of the DSL amplifier and an output in communication with the input of the low noise amplifier. In yet another embodiment, the Offset Cancellation Loop comprises: an OCL amplifier having an input in communication with the second output of the low noise amplifier and having an output; an OCL chopped switch having an input in communication with the output of the OCL amplifier and having an output; a high pass filter having an input in communication with the output of the OCL chopped switch and having an output; and an gain chopped switch having an input in communication with the output of the high pass filter and having an output in communication with the input of the low noise amplifier.

In another aspect, the invention relates to an autozero amplifier circuit cell. In one embodiment, the autozero amplifier circuit cell an autozero amplifier cell having an input in communication with a signal source and having an output; a low noise amplifier having an input in communication with the output of the autozero amplifier cell, a first output and a second output; an Impedance Boosting Loop including a IBL chopper switch having an input in communication with the low noise amplifier output and an output in communication with the low noise amplifier input; a DC Servo Loop including: a DSL amplifier having an input in communication with the output of the low noise amplifier; a DSL chopper switch having an input in communication with the output of the DSL amplifier and a output in communication with the input of the low noise amplifier; and an Offset Cancellation Loop including: an OCL amplifier having an input in communication with the second output of the low noise amplifier and having an output; an OCL chopped switch having an input in communication with the output of the OCL amplifier and having an output; a high pass filter having an input in communication with the output of the OCL chopped switch and having an output; and an gain chopped switch having an input in communication with the output of the high pass filter and having an output in communication with the input of the low noise amplifier. In another embodiment, the Impedance Boosting Loop comprises a IBL chopper switch having an input in communication with the low noise amplifier output and an output in communication with the low noise amplifier input. In still yet another embodiment, the DC Servo Loop includes: a DSL amplifier having an input in communication with the output of the low noise amplifier; a DSL chopper switch having an input in communication with the output of the DSL amplifier and an output in communication with the input of the low noise amplifier. In an embodiment, the Offset Cancellation Loop includes: an OCL amplifier having an input in communication with the second output of the low noise amplifier and having an output; an OCL chopped switch having an input in communication with the output of the OCL amplifier and having an output; a high pass filter having an input in communication with the output of the OCL chopped switch and having an output; and an gain chopped switch having an input in communication with the output of the high pass filter and having an output in communication with the input of the low noise amplifier.

In still yet another aspect, the invention relates to a bandpass filter. In one embodiment, the bandpass filter includes: a plurality of LUTs, each LUT having a plurality of inputs and having an output, a plurality of bit shift registers, each bit shift register having an input in communication with a digital signal source and an output in communication with a respective input of the plurality of inputs of the LUT; a summer having a first input in communication with the output of the LUT and having a second input and an output; and a register having an input in communication with the output of the summer and having an output in communication with the second input of the summer; wherein the output of the bandpass filter is the output of the register. In another embodiment, each LUT is a distributed quad-LUT.

BRIEF DESCRIPTION OF THE DRAWINGS

The structure and function of the invention can be best understood from the description herein in conjunction with the accompanying figures. The figures are not necessarily to scale, emphasis instead generally being placed upon illustrative principles. The figures are to be considered illustrative in all aspects and are not intended to limit the invention, the scope of which is defined only by the claims.

DESCRIPTION OF AN EMBODIMENT OF THE INVENTION

Figure 1:
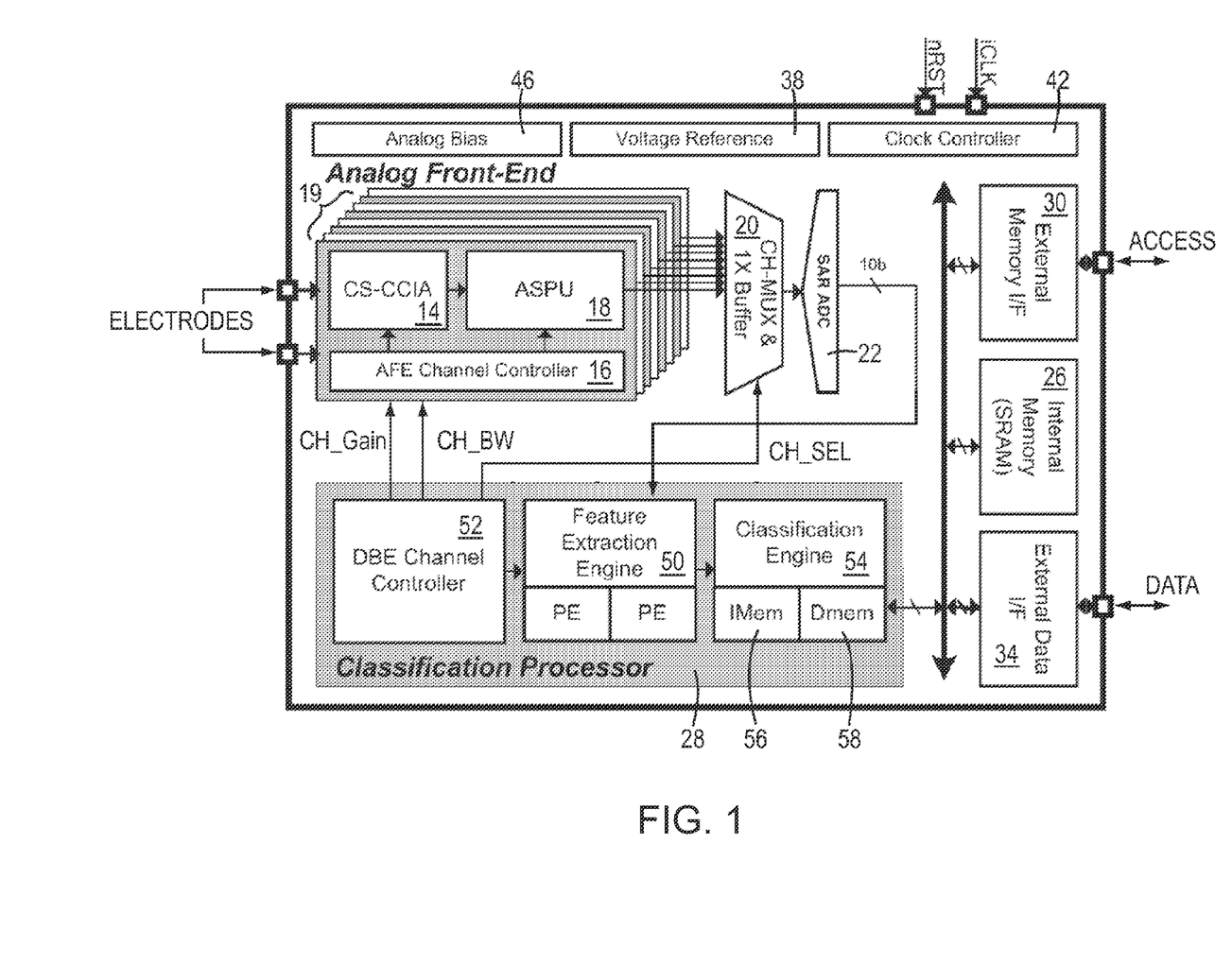
FIG. 1 is a block diagram of an embodiment of a Scalable EEG SoC constructed in accordance with the invention.

In brief overview, FIG. 1 discloses a block diagram of an embodiment of the scalable EEG SoC 10 constructed as interconnected integrated circuit cells (generally "cells") in accordance with the invention. This embodiment includes eight Analog Front-End processor cells (collectively 19). Two electrodes, configured as a differential pair, connect to one Analog-Front-End to form one channel. The eight Analog Front-End cells accommodate a total of 16 electrodes. Each Analog Front-End 19 cell includes a continuous-time Chopper Stabilized-Capacitive Coupled Instrumentation Amplifier (CS-CCIA) 14, an AFE Channel Controller 16, and a digitally-assisted reconfigurable Analog Signal Processing Unit (ASPU) 18. Each Analog Front-End cell 19 is connected to a respective input of a multiplexer cell 20. The output terminal of the multiplexer 20 is connected to the input of a ten bit SAR ADC cell 22 digitizing at a rate of 4K samples/sec/channel and whose output value is an input value to a patient-specific machine-learning seizure Classification Processor 28. The Classification Processor 28 includes a number of Feature Extraction Engine (FEE) processor cells 50, a Digital Back End (DBE) Channel Controller cell 52 and a Classification Engine (CE) cell 54. The CE 54 includes internal system memory interfaces (IMem) 56 for system instructions and (DMem) 58 for cache or data access to SRAM 26 and external memory, as described below. The IMem 56 and DMem 58 allow the SoC 10 to see both internal memory 26 and optional external memory as if they were a single unified storage.

The SoC 10 includes an SRAM cell 26 for storing data, an external memory interface cell 30 for allowing access to external memory and an external data interface cell 34 to permit external access to the data memory 26, debugging and the setting of certain system parameters, such as the number of channels, using configuration pins in the external data interface 34. These three cells are in communication with a bus that is in turn in communication with the Classification Processor 28 generally, and the DBE Controller 52, Feature Extraction Engine 50 and Classification Engine 54, specifically. The SoC 10 further has a voltage reference cell 38 that provides reference voltages to the SAR ADC 22, a clock controller cell 42 that divides the external one MHz clock signal to provide the necessary clock signals to the other cells and an analog bias circuit cell 46 to provide accurate bias voltages to the Analog Front-Ends 19.

Three control lines: Channel Gain (CH_GAIN), Channel Bandwidth (CH_BW) and Channel Select (CH_SEL) provide input values to both the Analog Front-End (AFE) controller 16 and channel selection in the multiplexer 20 respectively. These control lines are set by DBE Channel Controller 52 of the Classification Processor 28. In addition, the number of channels actually to be used (1, 2, 4, or 8) is set using the configuration pins of the external data interface 34 that in turn set values for the number of channels in the DBE Channel Controller 52. The DBE Channel Controller 52 then sets the AFE Channel Controller for the unused channels to "OFF" through a channel number select line. The system is configured to use the number of channels as needed in ascending order. That is if 4 channels are required the first 4 channels (1-4) are used.

In operation, generally, each EEG signal from a respective differential pair of a group of electrodes attached to the head of a patient is an input signal to a respective one of Analog Front-End processor cells 19 through the CS-CCIA cell 14. The CS-CIA is a low noise amplifier with a 4 KHz bandwidth described in more detail below. The resulting amplified EEG signal is an input signal to the ASPU 18. The ASPU 18 adapts the gain of the signal and limits the bandwidth of the EEG signal to 4 KHz. The signal processing of the ASPU 18 is discussed in more detail below. The output signals of all eight of the ASPU cells 19, each of which is also referred to as a channel, pass to the multiplexer 20 which selects the data channel to be passed to the SAR ADC 22.

One of the channels at a time is selected by a channel select CH_SEL control line asserted by the DBE Channel Controller 52. The selected channel data is digitized by the SAR ADC cell 22 using ⅛ of the time allowed for sampling all eight Analog Front-End 19 cells at 4K Hz/channel. The SAR samples at 4K Hz/sec/channel and will increase its digitization rate to meet this requirement. The multiplexer 20 will increase its scan rate of the channels to track the rate of digitization by the SAR 22. The 10 bit digitized value of the EEG signal from the SAR ADC 22 is the input value to the Feature Extraction Engine (FEE) (generally 50) through a classification multiplexer (not shown). The classification multiplexer takes the value of the sampled channel from the SAR ADC 22 and passes it to one of the eight processor elements (only two shown for clarity in FIG. 1) which make up the FEE 50. That is, each channel is assigned to and provides input data to one FEE processor element.

The 10 bits data from the selected channel entering the Feature Extraction Engine processor element 50 from the SAR ADC 22 are decimated by a decimation filter 96. The decimation filter 96 down-samples the 4K samples/sec being provided by the SAR ADC 22 by eight to produce 500 samples/sec of signal that is stored in the SRAM 26 and by 32 to produce the 128 samples/sec that will be utilized by the FEE processor element 19. This is done because the data rate of the SAR ADC 22 over samples compared to what is necessary for feature extraction. In other embodiments, the SAR ADC 22 is replaced with a standard ADC. Further, one embodiment does not use the decimation filter 96 and instead connects the bandpass filters 100 directly to the SAR ADC 22 or the ADC.

The data from the decimation filter 96 is passed through seven bandpass filters (BPF) (generally 100), each of which passes a different 4 Hz of sample, termed a sub-band. That is, one BPF passes 0-4 Hz sub-band, the second passes 4-8 Hz sub-band and so on. Each sub-band is then passed to a respective one of a series of integrators (generally 101) which integrates the sub-band over a 2 second interval to obtain the energy of the sub-band. The 10 bits of data from each sub-band are aggregated with the other sub-band data into 70 bits of channel data that is a feature vector for that channel. This feature vector is a feature vector without temporal information. By applying a triplet sliding window of the feature vector over time, an extracted feature vector (X) is formed that does have temporal information. The channel feature vectors is channel data and the channel data from the other seven FEE processors 19 are input to a multiplexer 108 of the CE 54.

The feature vector from each channel is input to the Support Vector Machine 54. The SVM also receives input from the classifier which has been trained using patient specific data 120. The SVM designates incoming feature vector from a channel as a seizure or non-seizure state by determining where the data falls relative to a six dimensional (corresponding to the seven frequency sub-bands) hyperplane that separates seizure and non-seizure regions of feature hyperspace. The SVM 112 classifies the incoming vector based in part on the patient specific parameters determined during training using data stored off-chip in a patient specific database. When a seizure condition is detected, the SVM sets a control line, CH_SEZ, high. This control line can then be used as a trigger for an alarm or other notification purpose.

It should be noted one electrode rather than a differential pair may be used. Further if less data is required, the SOC 10 can be constructed to measure an EEG with only one electrode rather than the sixteen electrodes just discussed thereby reducing the number of channels to one. In such a case, there is only one Analog Front End 19 required. Therefore, in this case, there is no multiplexer 20 required and the SAR DAC 22 can be connected to the output of the ASPU 18. Because there is only one channel, the Feature Extraction Engine 50 requires only one Feature Extraction Engine Processor.

Figures 2, 2A:
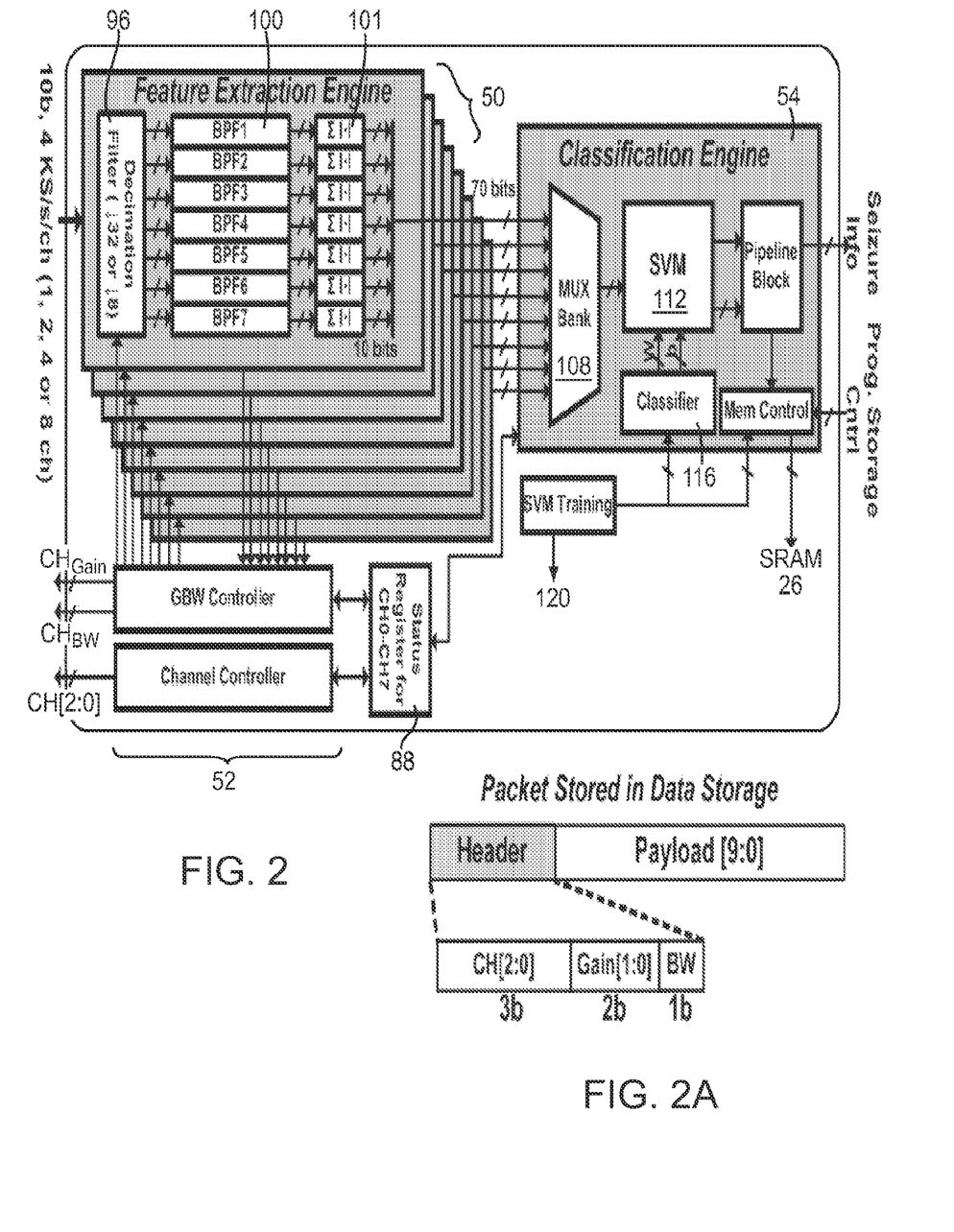
FIG. 2 is a block diagram of an embodiment of the Scalable EEG Classification Processor of FIG. 1.

Integrating eight-channel processing on a chip requires that both energy usage and area usage be performed efficiently. Considering some of the components in more detail, and referring to again to FIG. 2, the DBE Channel Controller 52 includes a Gain and Band Width Controller (GBW) 80 and a Channel Controller 84. The Channel Selector controls the selection of the channel through CH_SEL. DBE Channel Controller 52 also puts gain and bandwidth data in the Channel Status Register 88. This data is accessed by the CE 54 and is stored along with the EEG data when the EEG data is stored in SRAM 26. The CE 54 takes into account the current gain and bandwidth information of each channel from the status register 60 so the raw EEG can be recovered from the stored data accordingly. The format of the data storage is shown in FIG. 2a. The EEG data and control information is stored as a packet having a header that includes the channel number, the gain for the specified channel and the channel bandwidth. Once the channel gain and bandwidth data in the status register 88 are updated, the GBW controller 80 of the Classification Processor 28 configures ASPU 18 as discussed below. Again, in the case of a single EEG channel device, the DBE Channel Controller 52 no longer requires a CH_SEL control line because only one channel is used. Further, the data packet shown in FIG. 2a no longer requires a channel number as part of the header.

In a previous approach, digital band pass filters 100 of the FEE 50 were based on multiply-and-accumulate (MAC) operations that are power and area-consuming and that are avoided in the present design. In the present design, depending on the configured number of channels, the Classification Processor 28 through the DBE Channel Controller adapts the system clock speed in four steps to save power through the Clock Controller. With regard to area, an eight-channel Front-End 19 with filters occupies the majority of the area of the SoC. Analysis shows the filter bank alone may occupy up to 88.75% of the total chip area in the case of a parallel filter architecture, which is the main limiting factor for multi-channel integration.

In the present design, the multiply-and-accumulate operations of the prior filter designs are replaced with operations using a Look-Up-Table (LUT) to save processing power. The SoC 10 exploits a Distributed Quad-LUT (DQ-LUT) architecture shown in FIG. 3*a* using a four-input LUT partition for digital filter implementation. In this form of digital filter, one input is a fixed coefficient. Thus, the MAC operations can be replaced with a LUT and a knowledge of the other coefficient.

Figure 3A:
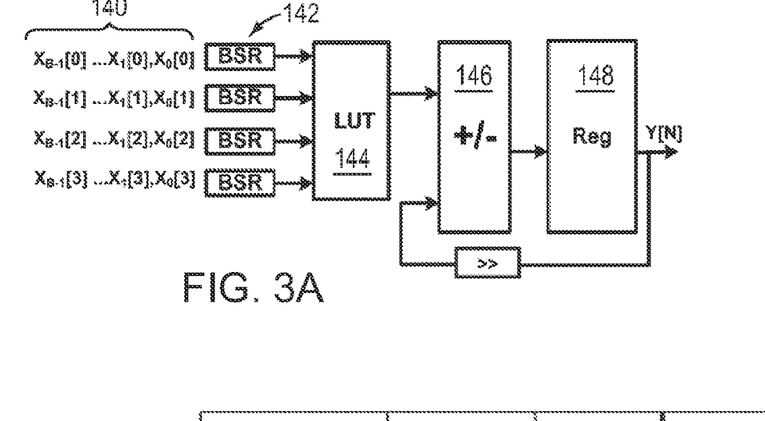
FIG. 3(a) is a block diagram of an embodiment of a single Distributed Quad-LUT filter cell constructed in accordance with the invention.

Generally and referring to FIG. 3(*a*), the $b^{th}$ bit of the $n^{th}$ sample ($X_b[n]$) (generally 140) from the SAR ADC 22 is an input to a respective bit shift register (BSR) 142 with one sample being assigned to each BSR 142. The bits pass through the BSRs 142 and are then processed by the LUT 144 so as to implement the function $f(C[n], X_b[n])$ where C is the fixed coefficient for the $n^{th}$ channel. Specifically:

$Y[N] = \Sigma 2^b \times \Sigma C[n] \times X_b[n]$ where $b$ ranges from 0 to $B-1$ and 0 to $n-1$ $Y[N] = \Sigma 2^b \times \Sigma f(C[n] \times X_b[n])$ where $b$ ranges from 0 to $B-1$ and 0 to $n-1$ The output of the LUT 144 is an input to a summer (+/−) 146 whose output is placed in a register 148 and fed back through a binary shift register as a second input to the summer 146. The output value from the register 148 is Y[N].

Figures 3B, 3C:
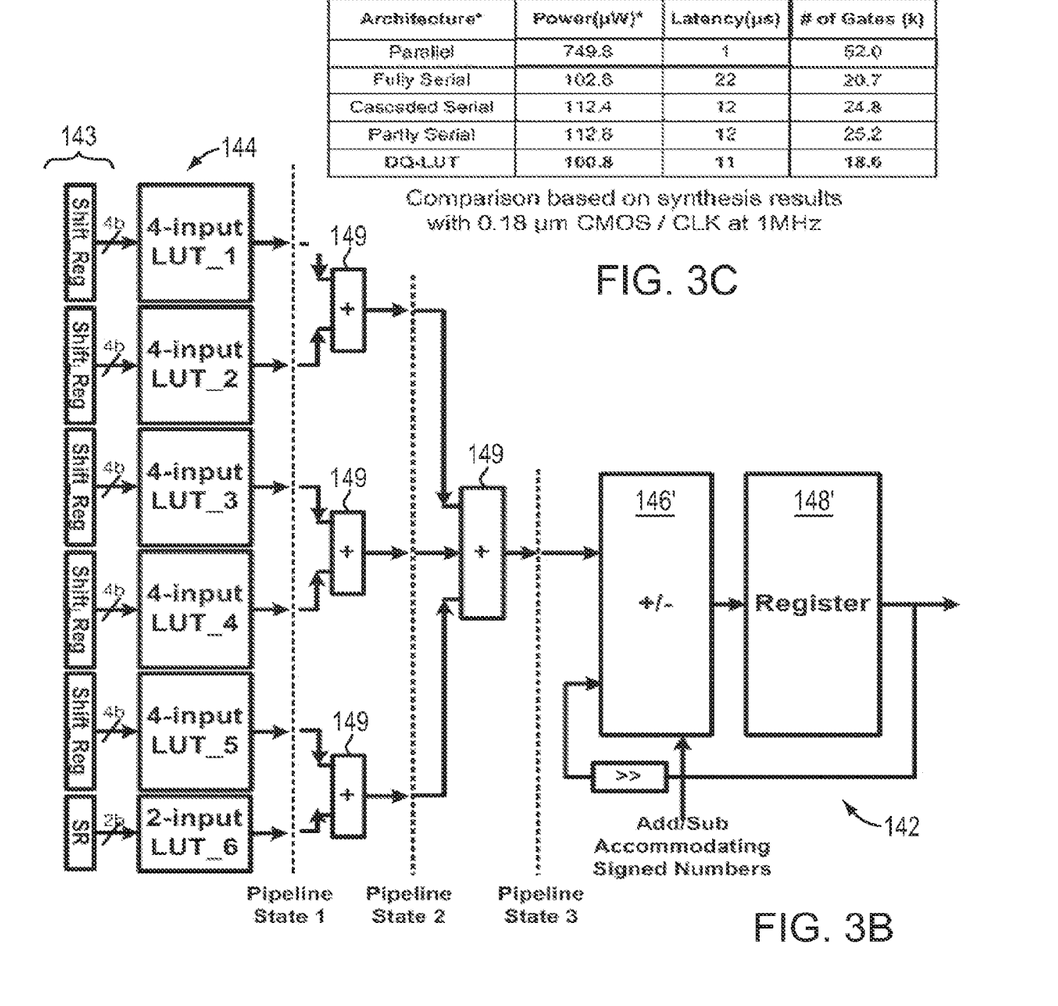
FIG. 3(b) is a block diagram of the single filter cell of FIG. 3a incorporated into a complete filter.
FIG. 3(c) is a comparison table of power consumption, latency and gate number for a variety of architectures.

The architecture shown in FIG. 3(*a*) is expanded as shown in FIG. 3(*b*) to perform the functions of one bandpass filter 142. The channel signal input from the decimation filter 96 is input to 5 four-input LUTs and a two-input LUT through shift registers 143. The results of the LUTs 144 are added (generally 149) and the resulting value input to a summer (+/−) 146' before being an input to the register 148'. As previously discussed, the output value of the register is Y[N] and the output value is also fed back to the second input of the summer 146' through a binary shift register. The advantage of using the LUT based system is demonstrated in FIG. 3(*c*), which shows the power consumed, latency and number of gates utilized for a number of different architectures. The power-delay-area product for the present device is reduced by 52.8% when compared with a parallel architecture. In other embodiments, the distributed quad-LUTs are replaced with LUTs. However, the use of the distributed quad-LUTs results in the lowest area-power-delay product.

Because the amplitude of an EEG signal during the clinical seizure onset phase tends to be significantly larger than it is during electrical seizure onset or during normal phase, the SoC 10 maintains high accuracy seizure detection by using the real-time gain and bandwidth (GBW) controller 58 (FIG. 2) to give feedback (CH_GAIN and CH_BW respectively) to the AFE Channel Controller 16 with respect to signal magnitude. Starting with a 52 dB AFE channel gain, the GBW controller 58 monitors each of ADC 22 output samples to determine into which sub-band it falls, and updates the GBW status register 88 every 2 seconds (FIG. 2).

Figure 4:
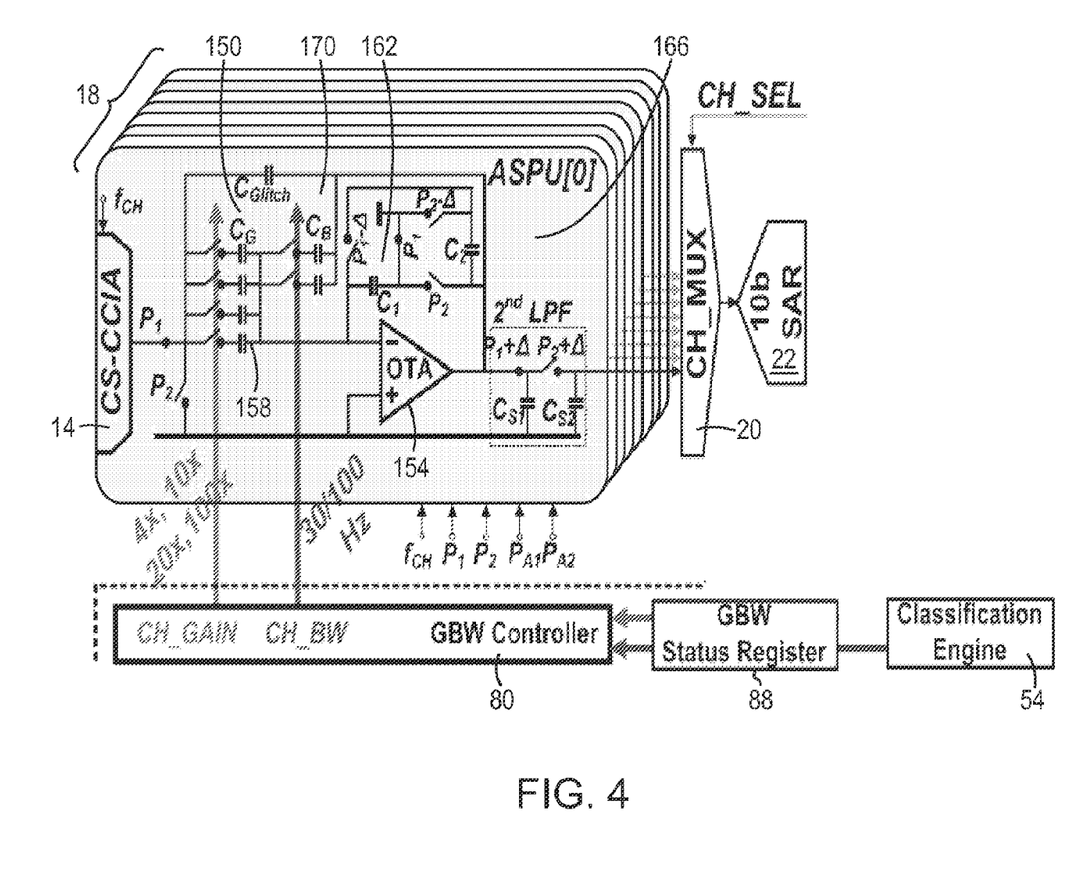
FIG. 4 is a block diagram of an embodiment of an ASPU for real-time AFE channel configuration of the Analog Front-End as shown in FIG. 1.

Referring now to FIG. 4, the Classification Processor 28 configures the ASPU 18 using the CE 54. At the core of each ASPU 18 lies an offset and finite-gain compensated switched capacitor (SC) amplifier that includes a plurality of switched capacitors 150 connected to one input of an operational transconductance amplifier 154. During Phase 1 ($\Phi_1$) when switches P1 are closed and switches P2 are open, the ASPU 18 samples the output values of the CS-CCIA 14 after the residual chopping spike has settled down sufficiently, and stores the voltage on gain control capacitors CG 158 (0.2 pF-5 pF). During Phase 2 ($\Phi_2$), when switches P2 are closed and switches P1 are open the corresponding charges on CG 158 are transferred to $C_1$ 162 (50 fF) and it is stored on $C_2$ 166 so that output voltage is close to $V_1$. ASPU 18 precisely controls AFE channel gain in four-steps (52 dB, 60 dB, 72 dB, 80 dB) to alter signal scale in advance of the interface with ADC 22. By programming the $C_B$ 170 value from 1.29 pF to 0.43 pF according to the seizure presence, ASPU 18 modifies the channel bandwidth of the AFE 19 from 100 Hz to 30 Hz with −40 dB/dec roll-off so that FEE 50 performs energy evaluation in seven spectral bands.

Figure 5A:
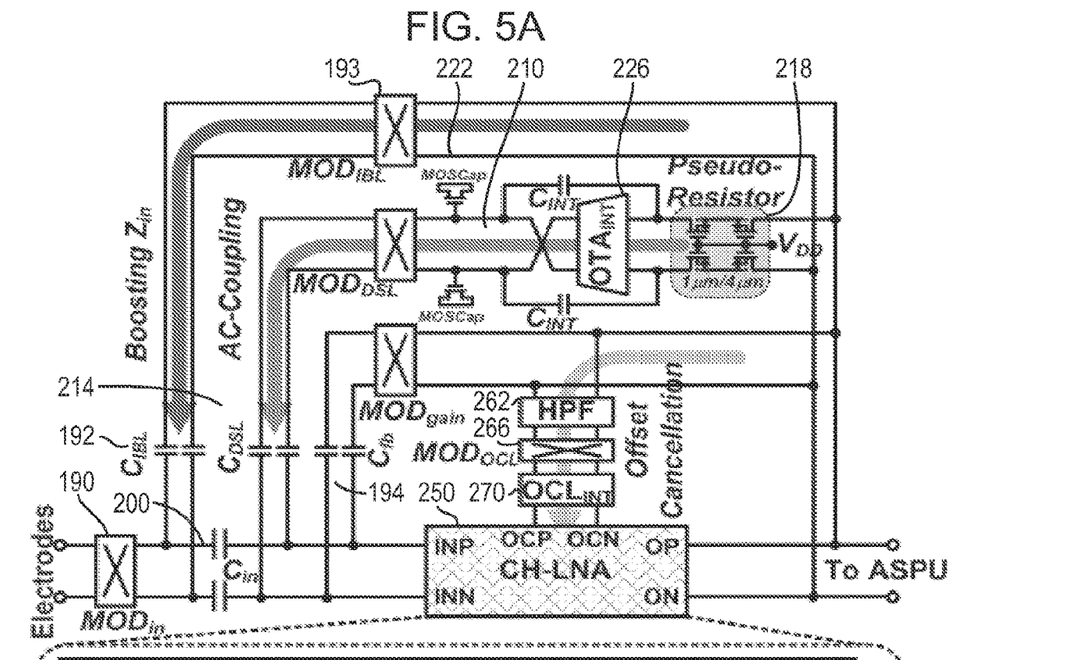
FIG. 5(a) is a block diagram of an embodiment of a CS-CCIA of the Analog Front-End as shown in FIG. 1.

Referring to FIG. 5(*a*), the fully-differential continuous-time CS-CCIA 14 is shown in more detail. The CS-CCIA includes an Offset Cancellation Loop, a DC Servo Loop and an Impedance Boosting Loop. The CS-CCIA directly modulates EEG signals using a chopper modulator ($MOD_{in}$) 190 for high common mode rejection ratios (CMRR). The differential Impedance Boosting Loop (IBL) compensates the input impedance degradation caused by the combination of the input chopper modulator ($MOD_{in}$) 190 and $C_{in}$, 200 so that CS-CCIA 14 maintains CMRR>90 dB even with 10 kΩ electrode mismatch. Using the capacitor $C_{IBL}$ 192 and the associated chopper switch 193 ($MOD_{IBL}$), some of the current from the CCIA is looped back to the input so that the input current driven by the electrode is decreased. By keeping the $C_{IBL}$ 192 equal to $C_{fb}$ 194 makes the boost factor equal to the gain of the CCIA. There are no active blocks in the IBL, and as a result, there is no extra power consumption. By using IBL loop, the 25 MΩ input impedance of a CS-CCIA can be boosted up to the Gf range. The result is a CMRR>90 dB even with an electrode impedance mismatch as great as 10 KΩ.

The DC Servo Loop (DSL) 210 filters out an Electrode DC Offset (EDO) through $C_{DSL}$, 214 which makes CS-CCIA 14 more power-efficient than what is used in the prior art. The DSL 210 should have a bandwidth of <20 MHz to achieve 0.5 Hz high-pass corner and a large EDO filtering range. This imposes a raised noise level or large area consumption. To overcome these issues, the DSL 210 introduces P-channel metal-oxide semiconductor (PMOS) off-state pseudo-resistors 218 (equivalent resistance>>10 TΩ) with only 10 pF (Metal-Insulator-Metal) MIM capacitor to extract DC offset from CS-CCIA 14 output; MOS capacitors 222 at output of operational transimpedance amplifier ($OTA_{INT}$) 226 store the DC offset voltage to counteract the EDO and filter out additional noise from $OTA_{INT}$ 226.

Figure 5B:
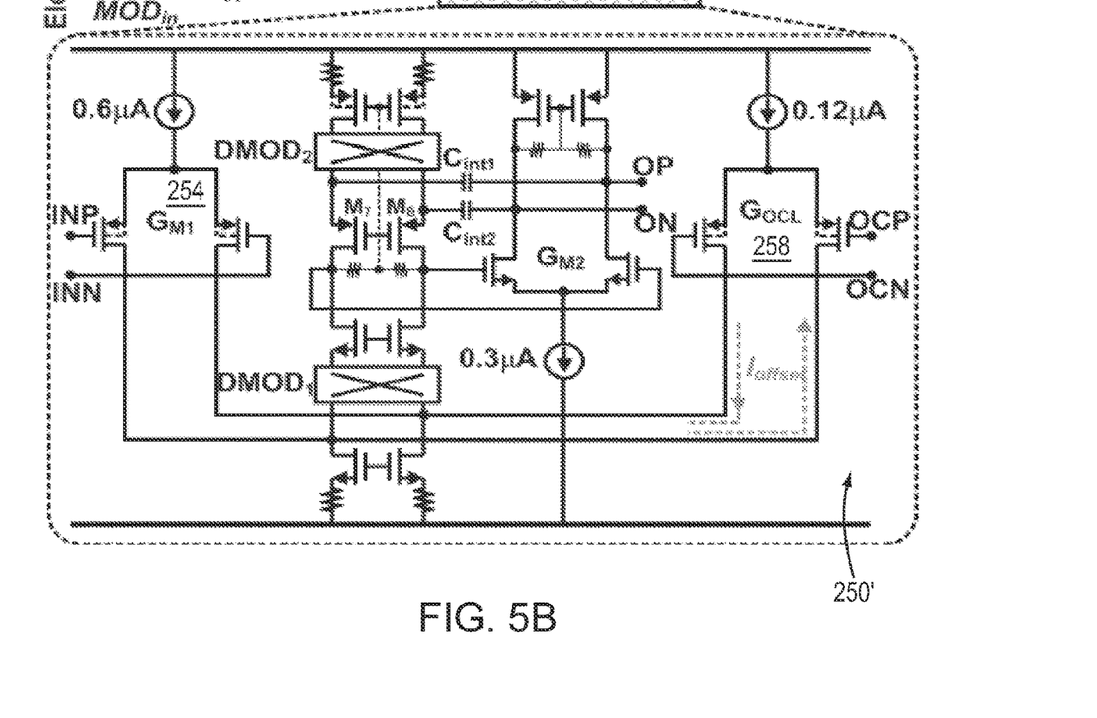
FIG. 5(b) is a schematic diagram of the Channel-low noise amplifier (CH-LNA) of FIG. 5(a)

To handle the EEG signal and the offset of CS-CCIA 14 simultaneously with power-efficiency, the CS-CCIA includes a Channel-low noise amplifier CH-LNA 250 (internal circuitry shown in FIG. 5(*b*)) that includes dual folded input pairs, $G_{M1}$ 254 and $G_{OCL}$ 258, respectively. Offset of CH-LNA 250 induces chopping ripple, which is then passed through high pass filter HPF 262, an offset cancellation chopper $MOD_{OCL}$ 266 and an Offset Cancellation Loop $OCL_{INT}$ 270 to generate $I_{offset}$ via $G_{OCL}$ 258. This $I_{offset}$ continuously cancels the CH-CCIA offset. A large $G_{M1}$ 254 (10×$G_{OCL}$) minimizes the noise elevation via $G_{OCL}$. 258. Because of the offset cancellation, CS-CCIA 14 has a >6 dB notch at the chopping frequency of 4 kHz, and this removes need for a complicated chopping spike filter or an area consuming low pass filter (LPF). When the DC Servo Loop (DSL) 210 is activated, the CS-CCIA 14 shows a HPF cut-off frequency of 70 MHz, and it elevates noise from 0.83 $\mu V_{rms}$ to 0.91 $\mu V_{rms}$. Compared with the previous integrated amplifiers (IAs), the fully-integrated CS-CCIA 14 enlarges the EDO filtering range up to ±200 mV which is a 4× improvement while consuming comparable power of only 2.5 µW.

In one embodiment, the CS-CCIA is replaced with an autozeroing amplifier circuit cell (not shown) which is identical to the CS-CCIA except that rather than modulate the EEG signals using the chopper $MOD_{in}$ 190, the chopper $MOD_{in}$ 190 is replaced with an autozero amplifier between the electrodes and the $C_{in}$ capacitors shown in FIG. 5(a).

Figure 6:
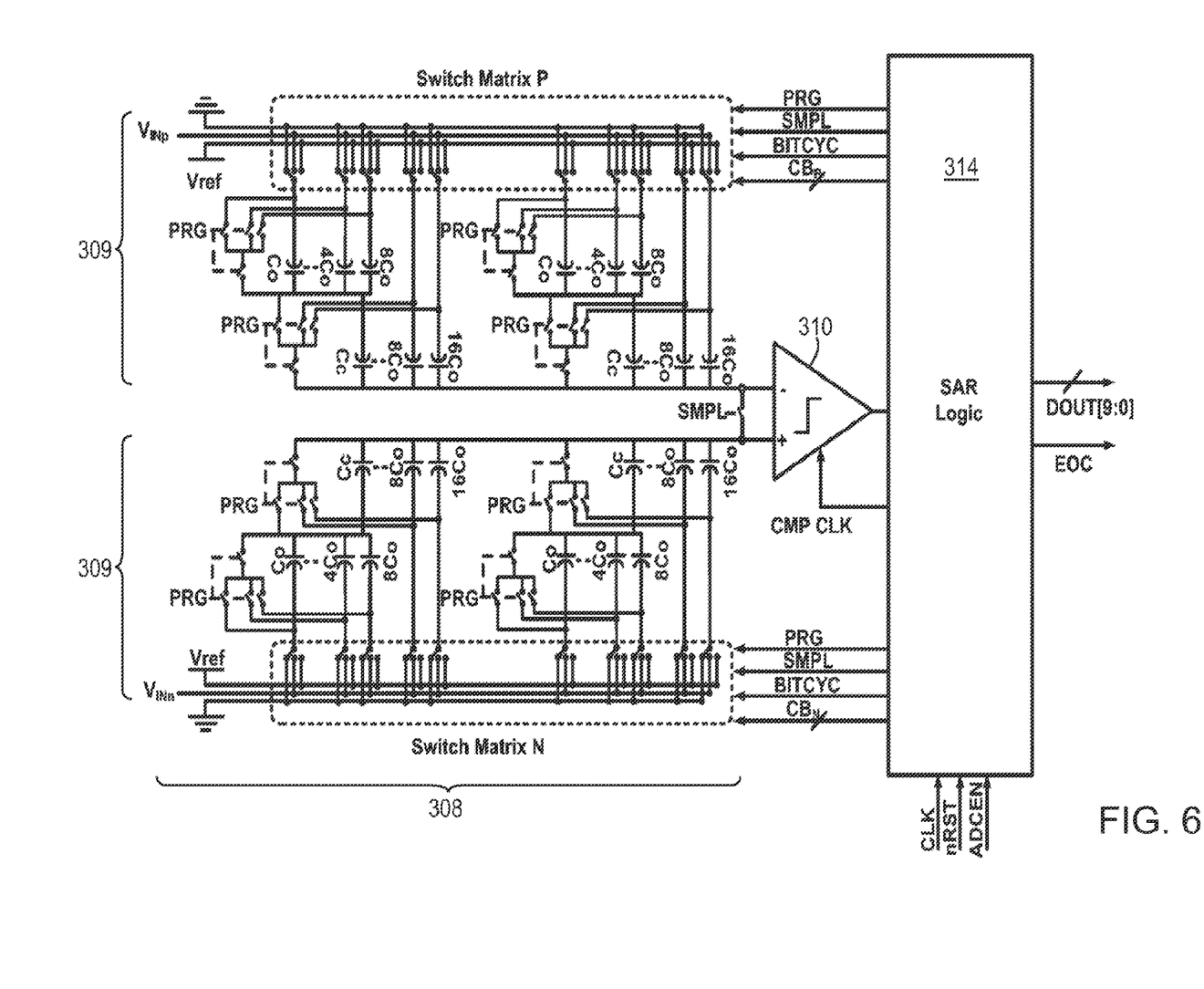
FIG. 6 is a schematic diagram of the SAR ADC cell.

Finally FIG. 6 is a schematic diagram of the SAR ADC cell 22. This embodiment is a ten bit ADC. The SAR ADC 22 includes a capacitive DAC 308 constructed of two sub-DACs 309, a digital comparator 310 and SAR logic 314. The outputs of the sub-DACs 309 are inputs to the comparator 310. The output of the comparator 310 is the input to SAR logic 314. The output value of the SAR logic is a ten bit digital value. The use of the two four bit sub-DAC and the split capacitor array again reduces area and power required by the cell.

The SoC 10 generally operates in 2 modes: a seizure detection mode and a recording mode. In the seizure detection mode, a bandwidth of 30 Hz is utilized with a 4-step adaptive channel gain according to the signal strength. Limiting the channel bandwidth to 30 Hz reduces the Front-End area required by the filter circuit by more than ⅔, thus leaving room for the Classification Engine 54 and the SRAM storage 26 to be integrated on-chip. Once a seizure is classified by the CE 54 and CH_SEZ is set high, the SoC 10 automatically runs in seizure recording mode at 100 Hz bandwidth to store the EEG data into the internal SRAM. In this recording mode both the Front-End 19 and CE 54 are turned off to save power. After a programmable period, the SoC returns to detection mode.

Figure 7:
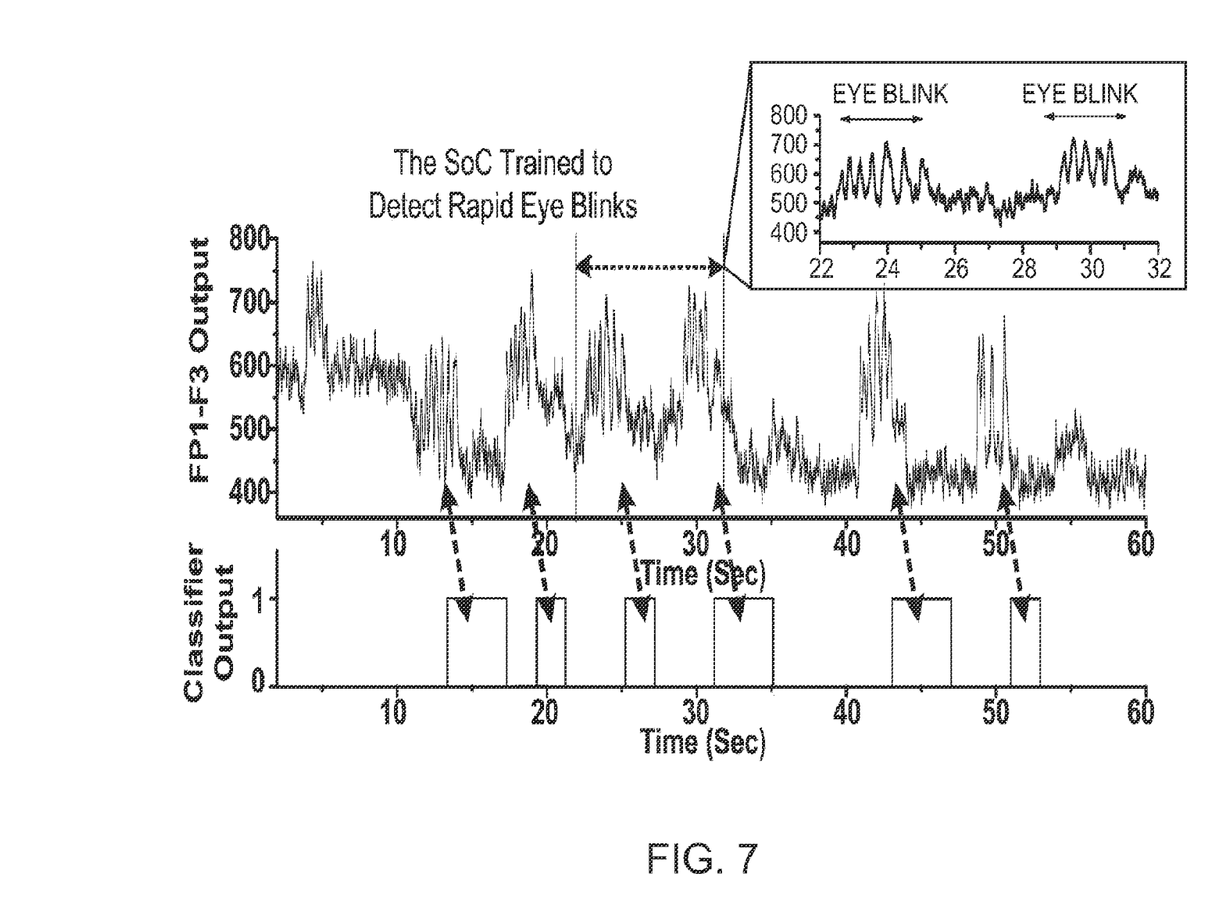
FIG. 7 depicts an EEG measurement with rapid-eye blink classification as measured by an embodiment of the invention.

FIG. 7 shows the results of an SoC 10 trained to detect rapid-eye blinks. Surface EEG electrodes of Fp1-F3 and Fp2-F4 with a common reference are used. The SoC 10 is trained to detect rapid-eye blinks pattern as this is similar to a generalized seizure. The SoC 10 successfully detects 84.4% of the cases within 2 seconds while consuming 2.03 uJ/classification at an 8-channel operation.

Figure 8A:
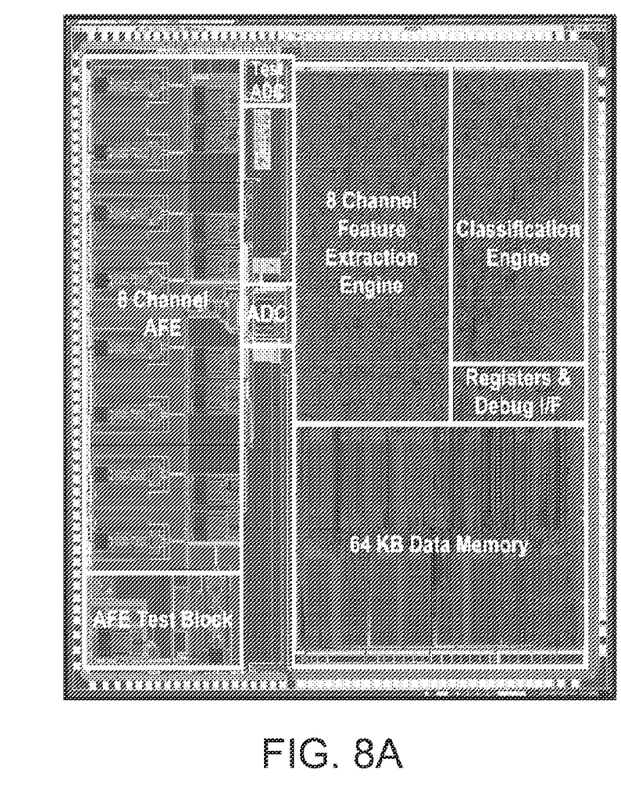
FIG. 8(a) is a micrograph of an embodiment of an SoC constructed in accordance with the invention.
Figure 8B:
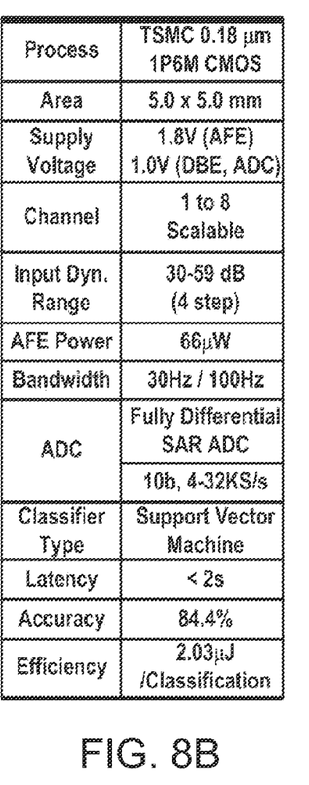
FIG. 8(b) is a performance summary of the SoC of FIG. 7.

FIG. 8 shows the performance summary of the SoC 10 with a micrograph of the chip. It advances state-of-the-art by fully-integrating instrumentation circuits, ADC, classification processor, and storage on a single 25 mm² chip (0.18 µm 1P6M standard CMOS) to continuously track patient-specific seizure activity.

It should be understood that the order of steps or order for performing certain actions is immaterial so long as the present teachings remain operable. Moreover, two or more steps or actions may be conducted simultaneously.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

The invention claimed is:

1. An electroencephalogram (EEG) monitor, comprising:
an integrated circuit chip comprising:
an Analog Front End cell, the Analog Front End cell comprising:
an amplifier cell in communication with an EEG electrode;
an analog signal processing unit (ASPU) cell in communication with the amplifier cell; and
a Classification Processor comprising:
a digital back end (DBE) Channel Controller cell;
a Feature Extraction Engine Processor cell, the Feature Extraction Engine Processor cell in communication with the DBE Channel Controller cell and the Analog Front End cell; and
a Classification Engine cell in communication with the Feature Extraction Engine Processor cell and the DBE Channel Controller cell; and
wherein a signal received from the electrode is processed by the Classification Engine cell and designated as seizure or non-seizure.

2. The EEG Monitor of claim 1 wherein the amplifier cell in communication with the electrode is a Chopper Stabilized-Capacitive Coupled Instrumentation Amplifier (CS-CCIA) cell.

3. The EEG Monitor of claim 1 wherein the amplifier cell in communication with the electrode is an autozeroing amplifier circuit cell.

4. The EEG Monitor of claim 1 wherein the Feature Extraction Engine Processor cell comprises:
a plurality of bandpass filter cells, each bandpass filter cell in communication with the ASPU cell; and
a plurality of integrator cells, each integrator cell in communication with a respective one of the plurality of bandpass filter cells;
wherein a signal from the ASPU cell of an Analog Front End is filtered by a plurality of bandpass filters to form a plurality of sub-bands, and
wherein each of the sub-bands is integrated by a respective one of the plurality of integrator cells to determine the energy of the sub-band.

5. The EEG Monitor of claim 4 wherein the Feature Extraction Engine Processor cell further comprises:
a decimation filter cell in communication between the ASPU cell and the plurality of bandpass filter cells; and
wherein a signal from the ASPU cell of an Analog Front End is decimated by the decimation cell prior to being filtered by the plurality of bandpass filter cells.

6. The EEG Monitor of claim 4 wherein the integrated sub-bands are aggregated to form a feature vector.

7. The EEG Monitor of claim 6 wherein the Classification Engine cell designates the signal received from the electrode as a seizure condition or a non-seizure condition in response to the feature vector.

8. The EEG Monitor of claim 1, wherein the integrated circuit chip further comprising an analog to digital converter cell in communication with the ASPU cell and the Feature Extraction Engine Processor cell.

9. The EEG Monitor of claim 8 wherein the analog to digital converter cell in communication with the ASPU cell and the Feature Extraction Engine Processor cell is a Successive-approximation-register analog-to-digital converters (SAR ADC).

10. The EEG Monitor of claim 7 wherein the Classification Engine comprises a support vector machine (SVM) and the SVM designates the signal, received from the electrode, as seizure or non-seizure in response to the feature vector, by determining on which side of a hyperplane in feature hyperspace the feature vector lies.

11. The EEG Monitor of claim 1:
wherein the Analog Front End cell is a plurality of Analog Front End cells,
wherein the Feature Extraction Engine cell is a plurality of Feature Extraction Engine cells, and
wherein each Feature Extraction Engine cell is in communication with a respective one of the Analog Front End cells.

12. The EEG Monitor of claim 11, wherein the integrated circuit chip further comprising:
a multiplexer cell in communication with the plurality of Analog Front End cells; and
an analog to digital converter (ADC) cell in communication with the multiplexer cell and the plurality of Feature Extraction Engine Processor cells.

13. The EEG Monitor of claim 12, where the ADC cell is a successive approximation register (SAR) cell.

14. The EEG Monitor of claim 1 wherein the DBE Channel controller comprises:
a channel gain control line and a channel bandwidth control line in communication with an Analog Front End cell.

15. The EEG Monitor of claim 12 wherein the DBE Channel Controller comprises:
a channel gain control line, a channel bandwidth control line, and a channel number select in communication with the Analog Front End (AFE) Channel Controllers and a channel select control line in communication with the multiplexer cell,
wherein the DBE Channel Controller is in communication with an external data interface, and
wherein the DBE Channel Controller selects the number of channel to be used in response to receiving the number of channels from the external data interface and setting the respective AFE Channel Controller on or off.

16. The EEG Monitor of claim 4, wherein each bandpass filter comprises:
a plurality of Look Up Tables (LUTs), each LUT having a plurality of inputs and having an output,
a plurality of bit shift registers, each bit shift register having an input in communication with the ASPU and an output in communication with a respective input of the LUT;
a summer having a first input in communication with the output of the LUT and having a second input and an output; and
a register having an input in communication with the output of the summer and having an output in communication with the second input of the summer;
wherein the output of the bandpass filter is the output of the register.

17. The EEG Monitor of claim 16 wherein the LUT is a distributed quad-LUT.

18. The EEG Monitor of claim 2 wherein the CS-CCIA comprises:
an input-chopped switch having an input in communication with the electrode and having an output;
a low noise amplifier having an input in communication with the output of the input-chopped switch and a first output connected to an input of the ASPU and having a second output;
an Impedance Boosting Loop (IBL) comprising a IBL chopper switch having an input in communication with the low noise amplifier output and an output in communication with the low noise amplifier input;
a direct current (DC) Servo Loop comprising:
a DC Servo Loop (DSL) amplifier having an input in communication with the output of the low noise amplifier;
a DSL chopper switch having an input in communication with the output of the DSL amplifier and a output in communication with the input of the low noise amplifier; and
an Offset Cancellation Loop (OCL) comprising:
an OCL amplifier having an input in communication with the second output of the low noise amplifier and having an output;
an OCL chopped switch having an input in communication with the output of the OCL amplifier and having an output;
a high pass filter having an input in communication with the output of the OCL chopped switch and having an output; and
a gain chopped switch having an input in communication with the output of the high pass filter and having an output in communication with the input of the low noise amplifier.

19. The EEG Monitor of claim 3 wherein the autozeroing amplifier circuit cell comprises:
an auto zero amplifier having an input in communication with the electrode and having an output;
a low noise amplifier having an input in communication with the output of the autozero amplifier and a first output connected to an input of the ASPU and having a second output;
an Impedance Boosting Loop (IBL) comprising a IBL chopper switch having an input in communication with the low noise amplifier output and an output in communication with the low noise amplifier input;
a direct current (DC) Servo Loop comprising:
a DC Servo Loop (DSL) amplifier having an input in communication with the output of the low noise amplifier;
a DSL chopper switch having an input in communication with the output of the DSL amplifier and a output in communication with the input of the low noise amplifier; and
an Offset Cancellation Loop (OCL) comprising:
an OCL amplifier having an input in communication with the second output of the low noise amplifier and having an output;
an OCL chopped switch having an input in communication with the output of the OCL amplifier and having an output;
a high pass filter having an input in communication with the output of the OCL chopped switch and having an output; and a gain chopped switch having an input in communication with the output of the high pass filter and having an output in communication with the input of the low noise amplifier.

20. The EEG Monitor of claim 1, wherein the integrated circuit chip further comprising:
a bus;
a static random-access memory (SRAM) in communication with the bus;
an external memory interface in communication with the bus; and
an external data interface in communication with the bus;
wherein the bus is in communication with the Classification Processor.

21. A method for monitoring an EEG comprising the steps of:
connecting an EEG electrode to an EEG monitor comprising an integrated circuit chip,
wherein the integrated circuit chip comprises:
an Analog Front End cell, the Analog Front End cell comprising:
an amplifier cell in communication with an EEG electrode;
an ASPU cell in communication with the amplifier cell; and
a Classification Processor comprising:
a DBE Channel Controller cell;
a Feature Extraction Engine Processor cell, the Feature Extraction Engine Processor cell in communication with the DBE Channel Controller cell and the Analog Front End cell; and
a Classification Engine cell in communication with the Feature Extraction Engine Processor cell and the DBE Channel Controller cell;
amplifying, via the integrated circuit chip, a signal from the EEG electrode to generate an amplified EEG signal;
adapting, via the integrated circuit chip, the gain of the amplified EEG signal using an ASPU;
digitizing, via the integrated circuit chip, the adapted gain signal using an analog to digital converter;
extracting, via the integrated circuit chip, a feature vector from the digitized adapted gain signal using a feature extraction engine; and
designating, via the integrated circuit chip, the feature vector as seizure or non-seizure using a classification engine.

22. The method of claim 21 wherein the step of adapting the gain of the amplified EEG signal occurs in real-time.

23. The method of claim 21 the step of extracting a feature vector comprises the steps of:
dividing the digitized adapted gain signal into a plurality of sub-bands;
integrating each sub-band to calculate the energy within each sub-band; and
aggregating each integrated sub-band to generate a feature vector.

24. The method of claim 21 wherein the step of designating the feature vector as seizure or non-seizure comprises the steps of:
generating, in response to patient data, a hyperplane separating a seizure region of feature hyperspace from a non-seizure region of feature hyper space; and
determining in which region of feature hyperspace the feature vector exists.

25. The method of claim 23 wherein the step of dividing the digitized adapted gain signal into a plurality of sub-bands utilizes a look up table (LUT).

* * * * *